US012280082B2

(12) United States Patent
Damle (10) Patent No.: US 12,280,082 B2
(45) Date of Patent: Apr. 22, 2025

(54) FORMULATION FOR INHIBITING VIRUS REPLICATION

(71) Applicant: Shibban Krishen Ganju, Oak Brook, IL (US)

(72) Inventor: Hrishikesh Damle, Bangalore (IN)

(73) Assignee: Shibban Ganju, Oak Brook, IL (US)

( * ) Notice: Subject to any disclaimer, the term of this patent is extended or adjusted under 35 U.S.C. 154(b) by 101 days.

(21) Appl. No.: 17/167,380

(22) Filed: Feb. 4, 2021

(65) Prior Publication Data

US 2022/0047663 A1    Feb. 17, 2022

(30) Foreign Application Priority Data

Aug. 12, 2020   (IN) .............................. 202041034650

(51) Int. Cl.
| | |
|---|---|
| *A61K 36/19* | (2006.01) |
| *A61K 31/40* | (2006.01) |
| *A61K 36/00* | (2006.01) |
| *A61K 36/23* | (2006.01) |
| *A61K 36/81* | (2006.01) |

(52) U.S. Cl.
CPC .............. *A61K 36/19* (2013.01); *A61K 31/40* (2013.01); *A61K 36/23* (2013.01); *A61K 36/81* (2013.01)

(58) Field of Classification Search
None
See application file for complete search history.

(56) References Cited

U.S. PATENT DOCUMENTS

| 8,673,331 | B2 * | 3/2014 | Cho ....................... A01N 59/16 424/443 |
| 11,931,390 | B1 * | 3/2024 | Rajendran .............. A61K 36/59 |
| 2006/0159784 | A1 * | 7/2006 | Ghosal .................... A61K 36/10 424/769 |
| 2014/0179602 | A1 * | 6/2014 | Weissman ................ A61L 2/00 514/13.5 |
| 2014/0187627 | A1 * | 7/2014 | Dai ....................... A61K 31/365 514/473 |
| 2014/0370092 | A1 * | 12/2014 | Parikh .................. A61K 9/2866 424/480 |
| 2021/0308232 | A1 * | 10/2021 | Tate ....................... A61K 47/02 |
| 2021/0308253 | A1 * | 10/2021 | Dorsey ................... A61P 37/04 |

FOREIGN PATENT DOCUMENTS

| CN | 1554370 | A | * | 12/2004 |
| IN | 201741002420 | A | * | 7/2018 |
| KR | 2017069026 | A | * | 6/2017 |
| RU | 2277932 | C2 | * | 6/2006 |

OTHER PUBLICATIONS

Buranasudja V, Rani D, Malla A, Kobtrakul K, Vimolmangkang S. Insights into antioxidant activities and anti-skin-aging potential of callus extract from *Centella asiatica* (L.). Scientific Reports. Jun. 29, 2021;11(1):13459.

Sharifi-Rad, J., Quispe, C., Ayatollahi, S.A., Kobarfard, F., Staniak, M., Stpień, A., Czopek, K., Sen, S., Acharya, K., Matthews, K.R. and Sener, B., 2021. Chemical Composition, Biological Activity, and Health-Promoting Effects of Withania somnifera for Pharma-Food Industry Applications. Journal of Food Quality, 2021, pp. 1-14.

* cited by examiner

*Primary Examiner* — Aaron J Kosar
*Assistant Examiner* — Randall O Winston
(74) *Attorney, Agent, or Firm* — JMB Davis Ben-David (57) ABSTRACT

The present invention is related to a novel formulation comprising active pharmaceutical ingredients, optionally in combination with other active pharmaceutical ingredients which are capable of inhibiting replication of the virus belonging to the family Coronaviridae. The present invention formulation includes *Andrographis paniculata*, PVP K30 and Acrylic polymer. The present invention further relates to different pharmaceutical formulations that have different modes of application.

5 Claims, 4 Drawing Sheets

FORMULATION FOR INHIBITING VIRUS REPLICATION

CROSS-REFERENCE TO RELATED APPLICATION

Benefit is claimed to Indian Patent Application number 202041034650, filed Aug. 12, 2020, the contents of which are incorporated by reference herein in their entirety.

FIELD OF THE INVENTION

The present invention relates to a pharmaceutical formulation comprising active pharmaceutical ingredients. More particularly, the present invention relates to a pharmaceutical formulation comprising of *Centella asiatica, Withania somnifera, Andrographis paniculata* for inhibiting replication of viruses belonging to family Coronaviridae.

BACKGROUND OF THE INVENTION

A virus is a submicroscopic infectious agent that replicates only inside the living cells of an organism. Viruses can infect all types of life forms, from animals and plants to microorganisms, including bacteria and archaea. Viruses spread in many ways. One transmission pathway is through disease-bearing organisms known as vectors: for example, viruses are often transmitted from plant to plant by insects that feed on plant sap, such as aphids; and viruses in animals can be carried by blood-sucking insects. Influenza viruses are spread by coughing and sneezing. Norovirus and rotavirus, common causes of viral gastroenteritis, are transmitted by the faecal-oral route, passed by contact and entering the body in food or water. Viral infections in animals provoke an immune response that usually eliminates the infecting virus. Immune responses can also be produced by vaccines, which confer an artificially acquired immunity to the specific viral infection. Some viruses, including those that cause AIDS, HPV infection, and viral hepatitis, evade these immune responses and result in chronic infections.

Pathogenic viruses pose very serious threat for the animals and human alike. If not controlled/treated, the diseases caused by viruses can become very serious. e.g. in 1918 flu pandemic was responsible for more than 100 million deaths and as per the reports of the WHO, the HIV has killed more than 25 million people since 1981. Recently, the pandemic caused by the Coronavirus has become very serious threat to the world.

The viruses of the family coronaviridae cause diseases in mammals and birds. In humans, coronaviruses cause respiratory tract infections that can range from mild to lethal. Mild illnesses include some cases of the common cold (which has other possible causes, predominantly rhinoviruses), while more lethal varieties can cause SARS, MERS, and COVID-19. Symptoms in other species vary: in chickens, they cause an upper respiratory tract disease, while in cows and pigs they cause diarrhea. Coronaviruses constitute the subfamily Orthocoronavirinae, in the family Coronaviridae, order Nidovirales, and realm Riboviria.

The viruses of family Coronaviridae replicates at very high rate and its morbidity rate is very high. Also, no vaccines or antiviral drugs to prevent or treat human coronavirus infections. However, the present invention provides novel formulation for the prevention of the replication of the virus related to the family Coronaviridae.

WO2007070986A1 discloses flavone compounds and their use in methods of treating or preventing parasitic infections, fungal infections and cell proliferative disorders. The present invention also relates to the use of flavone compounds in methods of controlling pests.

CN101987116A discloses a chinese medicinal extract for treating viral herpes and a preparation thereof. Liquorice and honeysuckle serving as main raw materials are subjected to extraction, and the extract can be taken orally or applied externally directly, or processed into granules for internal application, and spray or ointment for external application. The Chinese medicinal extract for treating the viral herpes and the preparation thereof have the effects of clearing heat, drying dampness, purging intense heat and removing toxin, can be applied to skin mucosa lesion, carbuncles and boils and the like, which are caused by toxic heat flourishing and dampness and heat internal obstruction symptoms, such as herpes zoster, hand-foot-and-mouth disease and the like.

CN110693974A discloses a traditional Chinese medicine preparation for preventing and treating African swine fever and a preparation method thereof. The invention can clear the blood poison in the live pig, eliminate the inflammation of the live pig, improve the immunity of the live pig, effectively prevent the diffusion of the African swine fever virus, has no adverse effect on the growth and development of the live pig, has better effect on various objects such as adult live pigs, piglets, sows and the like, has low cost of the implementation scheme, and can meet the requirements of the majority of pig farmers.

There is no indication from the existing art that the formulation comprising *Centella asiatica, Withania somnifera* and *Andrographis paniculata* are useful in the prevention of the replication of viruses belonging to family Coronaviridae. Therefore, the present invention discloses novel formulations useful in prevention of the replication of viruses belonging to family Coronaviridae. Hence there is a need of the present invention.

SUMMARY OF THE INVENTION

The present invention is related to a novel formulation comprising active pharmaceutical ingredients, optionally in combination with other active pharmaceutical ingredients which are capable of inhibiting replication of the virus belonging to the family Coronaviridae. The present invention formulation includes *Centella asiatica, Withania somnifera, Andrographis paniculata*, Starch, Magnesium stearate and K-30. The present invention further relates to different pharmaceutical formulations that have different modes of application.

In certain embodiment of the present invention, the present invention discloses a novel formulation comprising active pharmaceutical ingredients, optionally in combination with other active pharmaceutical ingredients which are capable of inhibiting replication of the virus belonging to the family Coronaviridae. The present invention formulation includes *Andrographis paniculata*, PVP K30 and Acrylic polymer. The present invention further relates to different pharmaceutical formulations that have different modes of application.

OBJECT OF THE PRESENT INVENTION

The main objective of the present invention is to have a novel pharmaceutical formulation based on *Centella asiatica, Withania somnifera* and *Andrographis paniculate*.

Another objective of the present invention is to have a novel pharmaceutical composition, the novel pharmaceutical composition comprises *Centella asiatica, Withania somnifera* and *Andrographis paniculate*.

Yet another objective of the present invention is to have a novel pharmaceutical formulation based on *Andrographis paniculate.*'

Yet another objective of the present invention is to inhibit replication of virus by using a novel pharmaceutical formulation.

Yet another objective of the present invention is to inhibit viral replication of virus belonging to family Coronaviridae.

Yet another objective of the present invention is to inhibit replication activity of microbes.

BRIEF DESCRIPTION OF THE DRAWINGS

The aforementioned aspects and other features of the present invention will be explained in the following description, taken in conjunction with the accompanying drawings, wherein.

DETAILED DESCRIPTION OF THE INVENTION

Unless otherwise defined herein, scientific and technical terms used in connection with the present disclosure shall have the meanings that are commonly understood by those of ordinary skill in the art. Further, unless otherwise required by context, singular terms shall include the plural and plural terms shall include the singular. Generally, nomenclatures used in connection with techniques of chemistry described herein are those well-known and commonly used in the art. In case of conflict, the present specification, including definitions, will control. The materials, methods, and examples are illustrative only and not intended to be limiting.

It must be noted that, as used in the specification and the appended claims, the singular forms "a," "an" and "the" include plural referents unless the context clearly dictates otherwise.

The term "comprising" as used herein is synonymous with "including" or "containing," and is inclusive or open-ended and does not exclude additional, unrecited members, elements or process steps.

The present invention relates to a novel pharmaceutical formulation for inhibition of replication of microbial pathogen. The present invention focused inhibiting replication of activity of viruses belonging to the family Coronaviridae, especially SARS-COV-2 The active ingredients of the present invention interact inhibit the replication activity of the virus. The novel formulation of the present invention comprises:

Centella Asiatica

*Centella asiatica*, commonly known as Indian pennywort or Asiatic pennywort, is an herbaceous, perennial plant in the flowering plant family Apiaceae. It is native to the wetlands in Asia. It is used as a culinary vegetable and as a medicinal herb. *Centella* grows in temperate and tropical swampy areas in many regions of the world. The stems are slender, creeping stolons, green to reddish-green in color, connecting plants to each other. It has long-stalked, green, rounded apices which have smooth texture with palmately netted veins. The leaves are borne on pericladial petioles, around 2 cm (0.79 in). The rootstock consists of rhizomes, growing vertically down. They are creamish in color and covered with root hairs. *Centella* contains pentacyclic triterpenoids, including asiaticoside, brahmoside, asiuyatic acid, and brahmic acid (madecassic acid). Other constituents include centellose, centelloside, and madecassoside.

Withania somnifera

*Withania somnifera* is a plant in the Solanaceae or nightshade family. Several other species in the genus *Withania* are morphologically similar. Although thought to be useful as a medicinal herb in Ayurveda, there is no conclusive clinical evidence that it is effective for treating any ailment. This species is a short, tender perennial shrub growing 35-75 cm (14-30 in) tall. Tomentose branches extend radially from a central stem. Leaves are dull green, elliptic, usually up to 10-12 cm (4 to 5 in) long. The flowers are small, green and bell-shaped. The ripe fruit is orange-red. The main phytochemical constituents are withanolides-which are triterpene lactones—withanolides, withaferin A, alkaloids, steroidal lactones, tropine, and cuscohygrine. Some 40 withanolides, 12 alkaloids, and numerous sitoindosides have been isolated. Withanolides are structurally similar to the ginsenosides of *Panax ginseng*, leading to a common name for *W. somnifera*, Indian *ginseng*.

Andrographis paniculata

*Andrographis paniculata*, commonly known as creat or green chireta, is an annual herbaceous plant in the family Acanthaceae, native to India and Sri Lanka. It is widely cultivated in Southern and Southeastern Asia, where it has been traditionally been believed to be a treatment for bacterial infections and some diseases. Mostly the leaves and roots were used for such purposes. The whole plant is also used in some cases. The species is distributed in tropical Asian countries, often in isolated patches. It can be found in a variety of habitats, such as plains, hillsides, coastlines, and disturbed and cultivated areas such as roadsides, farms, and wastelands. Native populations of *A. paniculata* are spread throughout south India and Sri Lanka which perhaps represent the center of origin and diversity of the species. The herb is an introduced species in northern parts of India, Java, Malaysia, Indonesia, the West Indies, and elsewhere in the Americas. The species also occurs in the Philippines, Hong Kong, Thailand, Brunei, Singapore, and other parts of Asia where it may or may not be native.

Starch

Starch or amylum is a polymeric carbohydrate consisting of numerous glucose units joined by glycosidic bonds. This polysaccharide is produced by most green plants as energy storage. It is the most common carbohydrate in human diets and is contained in large amounts in staple foods like potatoes, wheat, maize (corn), rice, and cassava. Pure starch is a white, tasteless and odorless powder that is insoluble in cold water or alcohol. It consists of two types of molecules: the linear and helical amylose and the branched amylopectin. Depending on the plant, starch generally contains 20 to 25% amylose and 75 to 80% amylopectin by weight. Glycogen, the glucose store of animals, is a more highly branched version of amylopectin. In the pharmaceutical industry, starch is also used as an excipient, as tablet disintegrant, and as binder.

Magnesium Stearate

Magnesium stearate is the chemical compound with the formula Mg (C18H35O2). It is a soap, 5 consisting of salt containing two equivalents of stearate (the anion of stearic acid) and one magnesium cation (Mg2+). Magnesium stearate is a white, water-insoluble powder. Its applications exploit its softness, insolubility in many solvents, and low toxicity. It is used as a release agent and as a component or lubricant in the production of pharmaceuticals and cosmetics.

Polyvinylpyrrolidone-K 30

Povidone-iodine (PVP-I), also known as iodopovidone, and polyvinylpyrrolidone, are antiseptics used for skin disinfection before and after surgery. It may be used both to disinfect the skin of the patient and the hands of the healthcare providers. It may also be used for minor wounds. It may be applied to the skin as a liquid or a powder.

Povidone-iodine is a broad-spectrum antiseptic for topical application in the treatment and prevention of wound infection. It may be used in first aid for minor cuts, grazes, burns, abrasions and blisters. Povidone-iodine exhibits longer lasting antiseptic effects than tincture of iodine, due to its slow absorption via soft tissue, making it the choice for longer surgeries. Chlorhexidine provides similar results, but with equal toxicity concerns.

Bacteria do not develop resistance to PVP-I.

Consequently, PVP-I has found broad application in medicine as a surgical scrub; for pre- and post-operative skin cleansing; for the treatment and prevention of infections in wounds, ulcers, cuts and burns; for the treatment of infections in decubitus ulcers and stasis ulcers; in gynecology for vaginitis associated with candidal, trichomonal or mixed infections. For these purposes PVP-I has been formulated at concentrations of 7.5-10.0% in solution, spray, surgical scrub, ointment, and swab dosage forms.

Acrylic Polymer

Acrylate polymers are a group of polymers prepared from acrylate monomers. These plastics are noted for their transparency, resistance to breakage, and elasticity. They are also commonly known as acrylics or polyacrylates. In the Acrylate polymer is commonly used in cosmetics, such as nail polish, as an adhesive and in the pharma industry acrylate polymers are used as film coating.

The present invention relates to a formulation for prevention of replication of microbes especially viruses. More particularly, the present invention relates to a pharmaceutical formulation for inhibiting viruses belonging to family Coronaviridae.

Accordingly, the present invention relates to a novel pharmaceutical formulation. The novel pharmaceutical formulation comprises *Centella asiatica, Withania somnifera, Andrographis paniculata*, Starch Magnesium stearate and PVP K 30. The *Centella asiatica*, the *Withania somnifera* and the *Andrographis paniculata* present in the novel pharmaceutical formulation are the principal ingredients, helps in inhibiting the replication of virus whereas the starch act as excipient, the magnesium stearate used as release agent and the PVP K 30 act as binder. In specific embodiment, the route of administration of the novel pharmaceutical formulation is oral. In particular embodiment, the novel pharmaceutical formulation is effective against inhibiting the replication of SARS-Cov-2 virus.

In certain embodiment of the present invention, the present invention relates to a novel pharmaceutical formulation. The novel pharmaceutical formulation comprises *Andrographis paniculata*, Polyvinylpyrrolidone-K 30 (PVP K 30) and acrylate polymer. The *Andrographis paniculata* present in the novel pharmaceutical formulation is the principal ingredient, helps in inhibiting the replication of virus whereas the PVP K 30 act as binder and the Acrylate polymer act as coating agent. In specific embodiment, the route of administration of the novel pharmaceutical formulation is oral. In particular embodiment, the novel pharmaceutical formulation is effective against inhibiting the replication of SARS-Cov-2 virus.

In certain embodiment of the present invention, the present invention relates to a novel pharmaceutical formulation. The novel pharmaceutical formulation comprises *Centella asiatica, Withania somnifera, Andrographis paniculata*, Starch, Magnesium stearate, PVP K 30 and Acrylate polymer. The *Centella asiatica, Withania somnifera, Andrographis paniculata* present in the novel pharmaceutical formulation helps in inhibiting the replication of virus whereas the starch act as excipient, the magnesium stearate used as a release agent, the PVP K 30 act as binder and the acrylate polymer act as coating agent. In specific embodiment, the route of administration of the novel pharmaceutical formulation is oral. In particular embodiment, the novel pharmaceutical formulation is effective against inhibiting the replication of SARS-Cov-2 virus.

In certain embodiment, the present invention relates to a novel oral pharmaceutical formulation. The novel oral pharmaceutical formulation comprises *Andrographis paniculata*, Polyvinylpyrrolidone-K 30 (PVP K 30) and Acrylate polymer. The *Andrographis paniculata* present in the novel oral pharmaceutical formulation helps in inhibiting the replication of virus whereas PVP K 30 act as binder and the Acrylate polymer act as coating agent. In particular embodiment, the novel oral pharmaceutical formulation is effective against inhibiting the replication of SARS-Cov-2 virus.

In certain embodiment of the present invention, the *Andrographis paniculata*, PVP and acrylate polymer are homogenously mixed and converted into granules.

In certain embodiment of the present invention, the granules lubricated with magnesium stearate.

In certain embodiment of the present invention, the granules containing the composition are filled in a capsule.

In certain embodiment of the present invention, the present invention relates to a novel oral formulation. The novel formulation comprises *Centella asiatica, Withania somnifera, Andrographis paniculata*, Starch, Magnesium stearate and PVP K 30. The *Centella asiatica, Withania somnifera, Andrographis paniculata* present in the novel oral formulation are the principal ingredients, helps in inhibiting the replication of virus belonging to family Coronaviridae whereas the starch act as excipient, magnesium stearate used as a release agent and PVP K 30 as binder. In specific embodiment, the novel oral formulation comprises 200 mg-600 mg of *Centella asiatica,* 100 mg-400 mg of *Withania somnifera,* 100 mg to 400 mg of *Andrographis paniculate,* 1 mg to 60 mg of starch, 1 mg to 50 mg of Magnesium stearate and 1 mg to 50 mg of PVP K 30. 3. The pharmaceutical formulation is for one or more capsules ranges between 300 mg to1000 mg.

In certain embodiment of the present invention, the present invention relates to a novel oral pharmaceutical formulation and delivery of the novel oral pharmaceutical formulation is through 500 mg capsule. The novel oral pharmaceutical formulation comprises *Centella asiatica, Withania somnifera, Andrographis paniculata*, Starch Magnesium stearate, and PVP K 30. The *Centella asiatica, Withania somnifera, Andrographis paniculata* present in the novel oral pharmaceutical formulation helps in inhibiting the replication of virus belonging to family Coronaviridae whereas the starch act as excipient, magnesium stearate act as a release agent and PVP K 30 act as binder. In specific embodiment, the novel oral pharmaceutical formulation comprises 200 mg of *Centella asiatica,* 100 mg *Withania somnifera,* 150 mg of *Andrographis paniculate,* 30 mg of starch, 10 mg of magnesium stearate and 10 mg of PVP K 30.

In certain embodiment of the present invention, the present invention relates to a novel oral pharmaceutical composition and delivery of the novel oral pharmaceutical composition is through 500 mg capsule. The novel oral pharmaceutical composition comprises *Centella asiatica, Withania somnifera, Andrographis paniculata,* Starch Magnesium stearate, and PVP K 30. The *Centella asiatica, Withania somnifera, Andrographis paniculata* present in the novel oral pharmaceutical composition helps in inhibiting the replication of virus belonging to family Coronaviridae whereas the starch act as excipient, magnesium stearate act as a release agent and PVP K 30 act as binder. In specific embodiment, the novel oral pharmaceutical composition comprises 200 mg of *Centella asiatica,* 100 mg *Withania somnifera,* 150 mg of *Andrographis paniculate,* 30 mg of starch, 10 mg of magnesium stearate and 10 mg of PVP K 30.

In certain embodiment of the present invention, the present invention relates to a novel oral formulation. The novel formulation comprises *Andrographis paniculata,* PVP K 30 and Acrylate polymer. The *Andrographis paniculata* present in the novel oral formulation is the principal ingredient, helps in inhibiting the replication of virus whereas PVP K 30 as binder and the Acrylate polymer act as coating agent. In specific embodiment, the novel oral formulation comprises 200 mg-600 mg *Andrographis paniculate,* 1 mg to 50 mg of PVP K 30 and 1 mg to 50 mg of Acrylic polymer.

In certain embodiment of the present invention, the present invention relates to a pharmaceutical formulation for sustainable release. The formulation composition comprising 480 mg of *Andrographis paniculate,* 10 mg of PVP K 30; and 10 mg of acrylate polymer. The pharmaceutical formulation inhibits the replication of viruses belonging to family Coronaviridae. The pharmaceutical formulation is lubricated with magnesium stearate. In the present invention, dosage of the pharmaceutical formulation is 500 mg. The pharmaceutical formulation is administered through oral route. In particular embodiment of the present invention the pharmaceutical formulation is administered through 500 mg capsule.

In certain embodiment of the present invention, the present invention relates to a pharmaceutical composition for sustainable release. The pharmaceutical composition comprising 480 mg of *Andrographis paniculate,* 10 mg of PVP K 30; and 10 mg of acrylate polymer. The pharmaceutical composition inhibits the replication of viruses belonging to family Coronaviridae. The pharmaceutical composition is lubricated with magnesium stearate. In the present invention, dosage of the pharmaceutical composition is 500 mg. The pharmaceutical composition is administered through oral route. In particular embodiment of the present invention the pharmaceutical composition is administered through 500 mg capsule.

In certain embodiment of the present invention, the present invention relates to a method for inhibiting, treating, or abrogating a SARS-COV-2 in a subject comprising administration of a novel pharmaceutical formulation. The novel pharmaceutical formulation comprises *Centella asiatica, Withania somnifera, Andrographis paniculata,* Starch, Magnesium stearate, PVP K 30 and Acrylate polymer. The *Centella asiatica, Withania somnifera, Andrographis paniculata* present in novel pharmaceutical formulation helps in inhibiting the replication of virus whereas the starch act as excipient, the magnesium stearate used as a release agent, the PVP K 30 act as binder and the acrylate polymer act as coating agent. In specific embodiment, the route of administration of the novel pharmaceutical formulation is oral. In particular embodiment, the novel pharmaceutical formulation is effective against inhibiting the replication of SARS-Cov-2 virus.

In certain embodiment of the present invention, the present invention relates to a method for preparation of pharmaceutical formulation used for inhibiting, treating, or abrogating a SARS-CoV-2 in a subject comprising administration of 480 mg of *Andrographis paniculata,* 10 mg of PVP K 30 and 10 mg of Acrylic polymer. The method includes sifting the material through the specified sieves given, transferring the material into a blender and mix well to obtain homogeneity, adding the PVP K 30 and Starch into the mixer and continue mixing to obtain granules. The acrylic polymer solution is sprayed over the granules, drying the wet mass in FBD, Passing the dry granules through the sieves to obtain final granules after the lubrication with magnesium stearate. The granules containing *Andrographis paniculata* act as an active principal ingredient filled in a capsule.

In certain embodiment of the present invention, the present invention relates to a method for preparation of pharmaceutical formulation. The method includes sifting the 480 mg of *Andrographis paniculate,* 10 mg of Polyvinylpyrrolidone-K 30 (PVP K 30) through sieves. Transferring the 480 mg of the *Andrographis paniculate* into a blender. Mixing the 480 mg of the *Andrographis paniculate* to obtain homogeneity. Adding the PVP K 30 and starch into the mixer for one or more granules formation. Spraying the acrylic polymer solution over the one or more granules. Drying the wet mixture in FBD. Lubricating the one or more granules with magnesium stearate. Passing the dried one or more granules through the sieves to obtain final one or more granules, wherein the one or more granules are filled in capsule. In particular embodiment, the one more granule are filled in 500 mg capsule.

In certain embodiment of the present invention, the present invention relates to a method for preparation of pharmaceutical composition. The method includes sifting the 480 mg of *Andrographis paniculate,* 10 mg of Polyvinylpyrrolidone-K 30 (PVP K 30) through sieves. Transferring the 480 mg of the *Andrographis paniculate* into a blender. Mixing the 480 mg of the *Andrographis paniculate* to obtain homogeneity. Adding the PVP K 30 and starch into the mixer for one or more granules formation. Spraying the acrylic polymer solution over the one or more granules. Drying the wet mixture in FBD. Lubricating the one or more granules with magnesium stearate. Passing the dried one or more granules through the sieves to obtain final one or more granules, wherein the one or more granules are filled in capsule. In particular embodiment, the one more granules are filled in 500 mg capsule.

In certain embodiment of the present invention, the novel capsule formulation of the comprises *Andrographis paniculata,* PVP K 30 and Acrylate polymer. The *Andrographis paniculata* present in the novel capsule formulation helps in inhibiting the replication of virus whereas the PVP K 30 act as binder and the acrylate polymer act as coating agent. In particular embodiment of the present invention the route of administration of the novel formulation is oral.

In certain embodiment of the present invention, the present invention relates to a novel oral formulation and delivery of the novel oral formulation through a 500 mg capsule. The novel oral formulation comprises *Andrographis paniculata*, PVP K 30 and Acrylate polymer. The *Andrographis paniculata* present in the novel oral formulation helps in inhibiting the replication of virus whereas the PVP K 30 act as binder and the acrylate polymer act as coating agent. In specific embodiment, the novel oral formulation comprises 480 mg of the *Andrographis paniculate*, 10 mg of the PVP K 30 and 10 mg of the acrylate polymer.

In certain embodiment of the present invention, the present invention relates to a novel pharmaceutical formulation. The novel pharmaceutical formulation comprises *Andrographis paniculata*, PVP K 30 and Acrylate polymer. The *Andrographis paniculata* present in the novel pharmaceutical formulation helps in inhibiting the replication of virus whereas the PVP K 30 act as binder and the acrylate polymer act as coating agent. In specific embodiment, the mode of administration of the novel pharmaceutical formulation is through tablet.

In certain embodiment of the present invention, the present invention provides a method for preparing novel formulation used for inhibiting virus replication, comprising contacting virus. The novel formulation comprises *Andrographis paniculata*, PVP K 30 and Acrylate polymer. The *Andrographis paniculata* present in the novel formulation helps in inhibiting the replication of virus whereas the PVP K 30 act as binder and the Acrylate polymer act as the coating agent whereby the novel formulation reduces, inhibits, or abrogates activity of a SARS-COV-2.

In certain embodiment of the present invention, the present invention provides a method of inhibiting, treating, or abrogating a SARS-COV-2 in a subject, comprising administering to a subject a novel formulation which comprises *Andrographis paniculata*, PVP K 30 and Acrylic polymer.

In certain embodiment of the present invention, the present invention provides a method for inhibiting virus replication, comprising contacting virus with novel formulation which comprises *Centella asiatica, Withania somnifera, Andrographis paniculata*, Starch, Magnesium stearate and PVP K 30 whereby the novel formulation reduces, inhibits, or abrogates activity of a SARS-COV-2.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions/formulation, the exemplary methods, devices, and materials are described herein. It is to be understood that this disclosure is not limited to particular methods, and experimental conditions described, as such methods and conditions may vary.

Figure 1A:
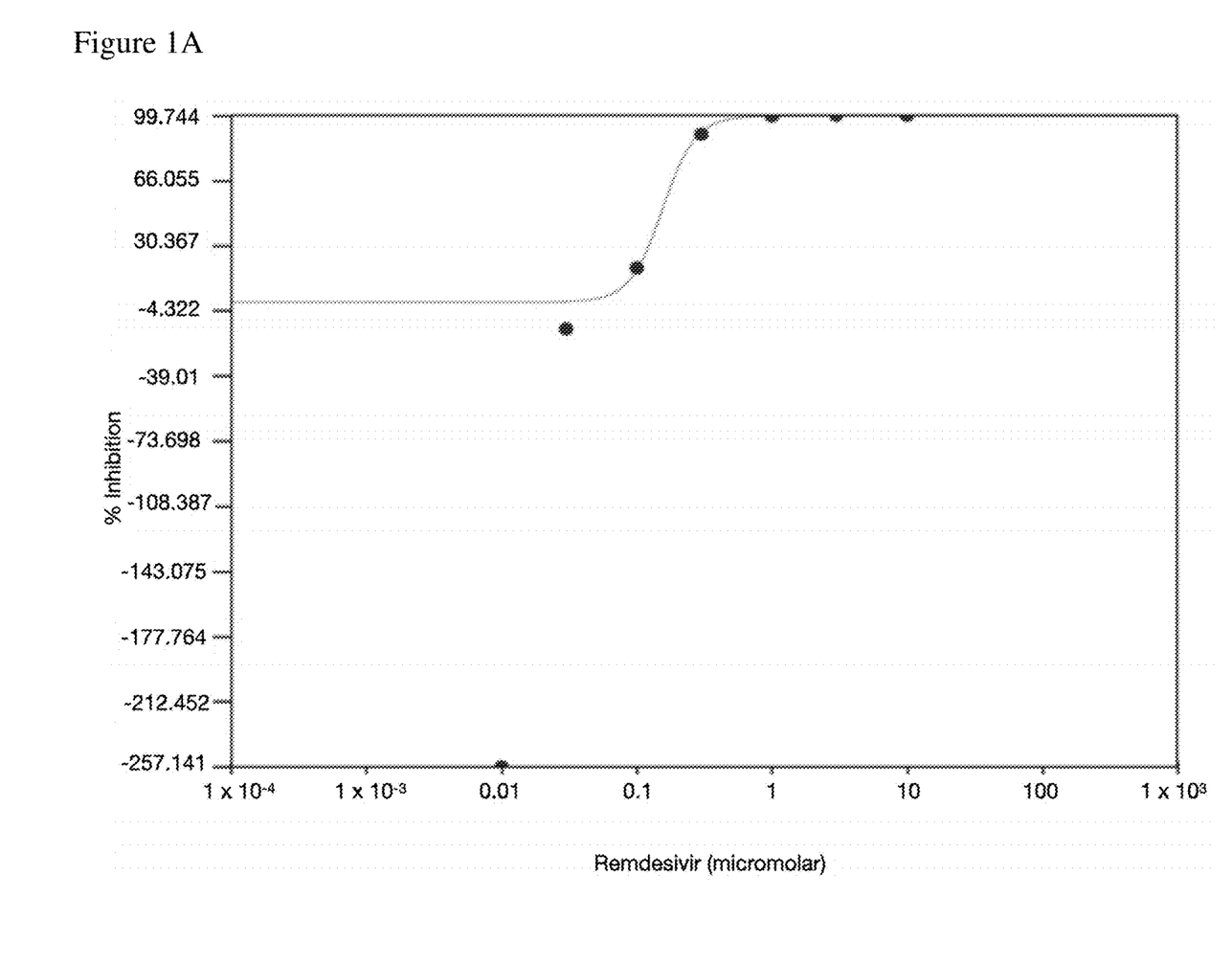
FIG. 1A illustrates dose dependent response of Remdesivir for SARS-COV-2 E gene in accordance with embodiments of the present invention.
Figure 1B:
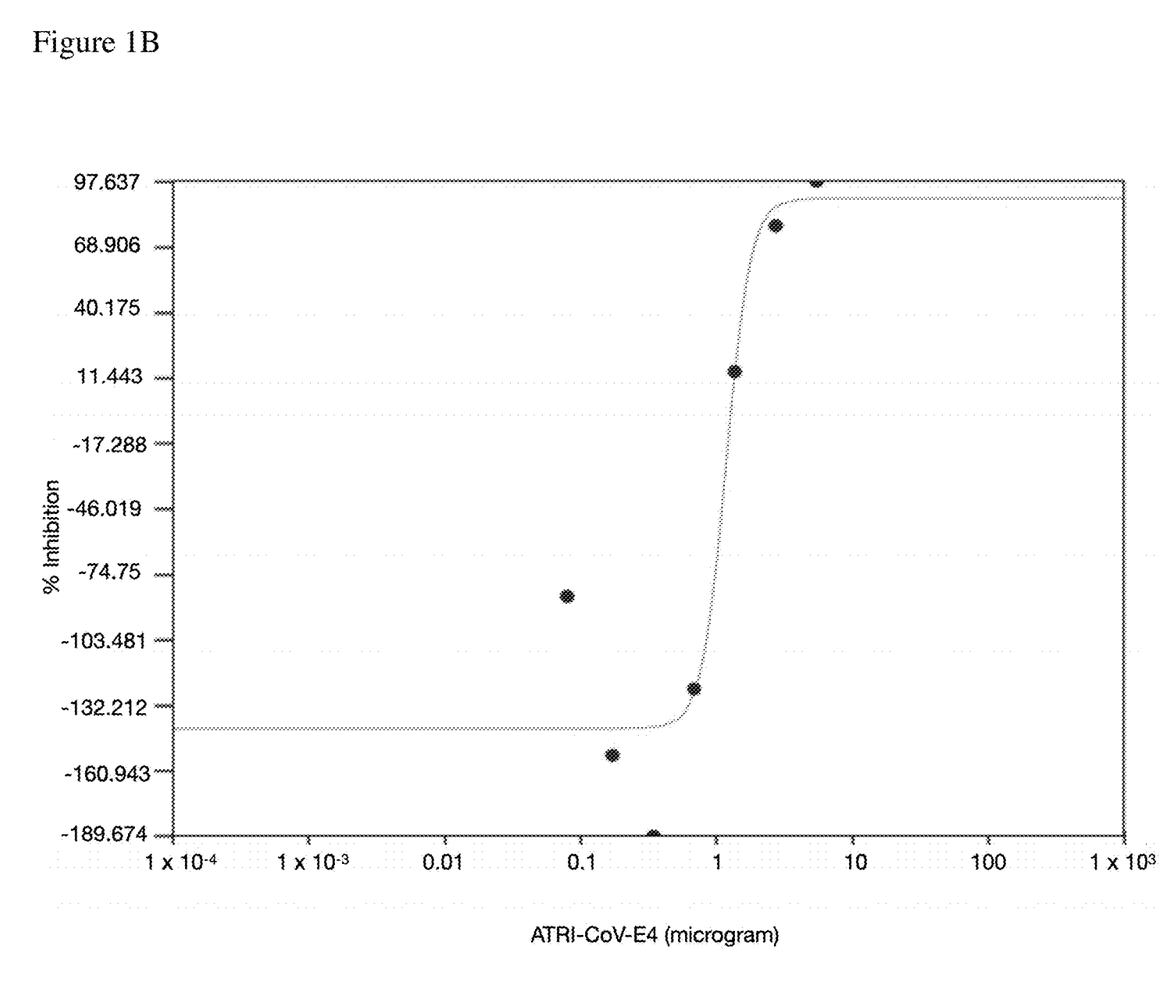
FIG. 1B illustrates dose dependent response of *Andrographis paniculata* for SARS-CoV-2 E gene in accordance with embodiments of the present invention.

1. Materials and Methods:

Applicant has a plant molecules database and the molecules in the database are the inputs for the screening of Anti-SARS-COV-2 molecules targeting SARS-COV-2 target proteins which having significant role in entry, replication and packing of SARS-COV-2 in host cell. Initially virtual screening of more than 4 Lakh plant small molecules against 6 potential SARS-COV-2 targets was performed using molecular docking technique as shown in FIG. 1.

1.1 Molecular Docking and MD Simulation

Virtual screening of small molecules in our library against 6 potential SARS-COV-2 targets such as Spike glycoprotein (S-Protein), Envelope Protein (E-Protein), RNA dependent RNA polymerase (RdRp), 3C-like protease (3CL-Pro), Papain-like protease (PLPro), and Main Protease (M-Pro) using Schrodinger small molecule suite. The crystal structure of 5 target proteins were retrieved from Protein Data Bank (PDB) except S-Protein and S-Protein structure was modelled using Swiss modeller. Molecular docking was performed at different precisions to accelerate the process speed and minimise the computational time.

The lead molecules in complex with target proteins were subjected for MD Simulation using Desmond MD simulation tool where root mean square deviation (RMSD) and root mean square fluctuation (RMSF) were considered as a major factors to measure the protein-ligand interaction stability. Resultantly, plant molecules for each targets were shortlisted and compiled for their Anti-SARS-COV-2 activity. The critical compilation of computational data has suggested the molecules in *Andrographis paniculate* as a potent Anti-SARS-COV-2 therapeutics and the same were investigated in vitro.

1.2. Extraction, Isolation and Purification of Plant Molecules

The *A. paniculate* identified as a potent Anti-SARS-COV-2 therapeutics was subjected for whole plant ethanol extraction using conventional bio separation techniques like soxhlation. The whole plant ethanol extract of *A. paniculate* (ATRI-CoV-E4) was subjected for in vitro cytotoxicity and Anti-SARS-COV-2 activity.

1.3. In Vitro Cytotoxicity

The cytotoxicity assay was done in a 96-well plate format in 3 wells for each sample. 1×10e4 VeroE6 cells were plated per well and incubated at 37° C. overnight for the monolayer formation. Next day, cells were incubated with 1 µl (5.5 mg/ml solution in 200 µl) *A. paniculate* at the concentration with final DMSO conc. being 0.5%. The control cells were incubated with 0.5% DMSO only. The cells without test substance was the control for water soluble compounds. 24 and 48 hours later, cells were stained with Hoechst 33342 and Sytox orange dye. Images were taken at 10×, 16 images per well, which covers 90% of well area using ImageXpress Microconfocal (Molecular Devices). Hoechst 33342 nucleic acid stain is a popular cell-permeant nuclear counterstain that emits blue fluorescence when bound to dsDNA. It stains all the live and dead cells. Sytox orange dye stains nucleic acids in cells with compromised membranes. This stain is an indicator of cell death. First, the software will count total number of cells in the Hoechst image. In the Sytox image, it will count, among Hoechst positive cells, how many cells are positive for sytox.

1.4. In Vitro Anti-SARS-COV-2 Activity

The assay was done in a 96-well plate format in 3 wells for each sample. 1×10e4 VeroE6 cells were plated per well and incubated at 37-degree C. overnight for the monolayer formation. Next day, cells were incubated with 1 µl (5.5 mg/ml solution in 200 µl) *A. paniculate* at the indicated concentration with final DMSO conc. being 0.5%. The control cells were incubated with 0.5% DMSO only. The cells without test substance was the control for water soluble compounds. The cells were infected with SARS-COV2 at a MOI of 0.01. 24 and 48 hours later, viral RNA was extracted from 100 µl culture supernatant and subjected to qRT-PCR (in duplicates) where Ct values for N and E gene sequence were determined. Inhibition of virus replication is determined based on the fold change in the Ct value in TS-treated cells compared to the control. Remdesivir was used as a positive control for viral inhibition.

1.5. In Vitro $IC_{50}$ Estimation

The assay is done in a 96-well plate format in 3 wells for each sample. 1×10e4 VeroE6 cells were plated per well and incubated at 37-degree C. overnight for the monolayer formation. Next day, cells were incubated with *A. paniculate* at the 7-point concentration. For Remdesivir, the following concentrations were used: 10, 3, 1, 0.3, 0.1, 0.03 and 0.01 μM. For *A. paniculate,* 5.5 mg/ml stock solution was serially diluted in DMSO (2-fold dilution). From each dilution, 1-microliter was used for drug screening assay. The 7-point concentrations of *A. paniculate* were 5.5, 2.75, 1.37, 0.68, 0.34, 0.17 and 0.08 μg. The control cells were incubated with 0.5% DMSO only. The cells were infected with SARS-COV2 at a MOI of 0.01. 48 hours later, viral RNA was extracted from 100 μl culture supernatant and subjected to qRT-PCR (in duplicates) where Ct values for N and E gene sequence were determined. Inhibition of virus replication is determined based on the fold change in the Ct value in TS-treated cells compared to the control. IC50 values were determined using AAT Bioquest IC50 calculator.

1.6. In Vivo Toxicity

The institutional Animal Ethical Committee (IAEC) approved in vivo acute and subacute toxicity studies for *A. paniculate* were performed using following test system.

1.6.1 Test System

The study was designed to use minimum possible number of animals to fulfil the objectives of the experiment, good scientific justification & requirements of regulatory guidelines. Selected females were nulliparous and non-pregnant. The individual body weight of animals was within ±20% of group mean body weight range.

Species: a) *Rattus norvegicus* (Rat)
b) *Mus musculus* (Mice)
Strain: a) Wistar
b) Swiss
Sex: Female
Age at the time of treatment: 6-8 Weeks
Body weight at the beginning of treatment: Rat: 220±22.07 g, Mice: 28.03±0.37 g
Source: In-house Animals 1.6.2 Preparation of Dose Formulation Test substance formulation (simple suspension) was prepared by standard procedure using mortar and pestle. Initially required quantity of the ATRICOV 452 for preparing 2000 mg/kg dose was weighed and placed in mortar and pestle. Then small quantity of water was added and sample was triturated using pestle. Once all sample is wet, remaining quantity of the water was added slowly with trituration process continued to get simple suspension. Formulation details are as below in Table 1.

TABLE 1

Details on test substances

| Test Substance | Dose (mg/Kg) | Test Item (mg) | Water (ml) | Dose volume (ml/kg) | Concentration of dosing solution (mg/ml) |
| --- | --- | --- | --- | --- | --- |
| *A. paniculate* | 2000 | 2500 | 5 | 4 | 500 |

1.7. Clinical Trials

In spite of known safety, the Phase-1 study entitled "A Prospective, Interventional, Open label, Phase 1, single-centre, single fasting dose study to evaluate the safety and tolerability of ATRICOV 452 capsule of 500 mg in healthy adult human subjects" is approved by CTRI and the study is underway in the CDSO-DCGI approved CRO located at Bangalore (India). The CRO has its own in-house ethical committee and the study is expected to be completed in late September. The Phase-2 study protocol design is completed and ready for CTRI submission.

2. Results 2.1 Molecular Docking and Phytochemical Extraction

Docking score is the indicator of ligand-protein interaction in molecular docking. The molecules is *A. paniculate* have shown fairly acceptable interaction with Anti-SARS-COV-2 drug targets as shown in Table 2. A few molecules in *A. paniculate* were identified as inhibitors of more than one drug target and offer the activity by polypharmacological activity.

TABLE 2

List of plant molecules in *A. paniculate* and their docking score to inhibit Anti-SARS-CoV-2 drug targets.

| Plant molecules | S-Protein | RdRp | 3CLPro | Mpro | E-Protein | PPLPro |
| --- | --- | --- | --- | --- | --- | --- |
| ATR1174480 | -3.801 | -8.122 | | | | |
| ATRI31729 | -3.627 | | | | | |
| ATRI156456 | -4.564 | | | | | |
| ATR1212130 | -2.571 | -8.306 | | | | |
| ATRI36128 | -3.888 | | | | | |
| ATR126097 | -2.672 | -8.222 | | | | |
| ATRI146227 | -3.875 | | | | | |
| ATRI59615 | -3.646 | | | | | |
| ATRI107948 | | | | | -8.326 | |
| ATRI183973 | -3.651 | | | | | |
| ATRI69996 | -3.860 | | | | | |
| ATRI50182 | -3.977 | | | | | |
| ATRI42096 | -4.253 | | | | | |
| ATRI149880 | -4.633 | -8.350 | -7.186 | -6.517 | | -4.498 |
| ATRI25112 | -3.418 | | | | | |
| ATRI48910 | -5.124 | | | -6.191 | | -4.273 |
| ATRI49046 | -3.311 | | | | | -4.983 |
| ATRI180181 | -4.453 | | | | | |

TABLE 2-continued

List of plant molecules in *A. paniculate* and their docking score to inhibit Anti-SARS-CoV-2 drug targets.

| Plant molecules | S-Protein | RdRp | 3CLPro | Mpro | E-Protein | PPLPro |
|---|---|---|---|---|---|---|
| ATRI224611 | -4.356 | -8.031 | -7.671 | -10.077 | | |
| ATRI132445 | -3.097 | | | | | |
| ATRI119364 | -3.103 | | | | -7.834 | |
| ATRI187760 | -3.546 | | | | | |
| ATRI73673 | -3.721 | -8.211 | | | | |
| ATRI88341 | -3.704 | | | | | |
| ATRI50940 | -3.664 | | | | | |
| ATRI24100 | -3.798 | | | | | |
| ATRI191216 | -3.843 | | | | | |
| ATRI156101 | -4.396 | | | | | |
| ATRI31817 | -3.573 | | | | | |
| ATRI96636 | -4.497 | | | -6.913 | | |
| ATRI36615 | -3.723 | | | | | |
| ATRI11020 | -2.084 | | | | | |
| ATRI181381 | -2.461 | -8.216 | | | | |
| ATRI226113 | -3.664 | -8.025 | | | | |
| ATRI27096 | -3.943 | | | | | |
| ATRI139970 | -3.107 | | | | -4.890 | |
| ATRI215998 | -3.614 | -8.262 | | | | |
| ATRI195437 | -3.386 | | | | | -5.708 |
| ATRI199640 | -2.653 | | | | | -4.238 |
| ATRI144162 | -4.284 | | | | | |
| ATRI116360 | -4.072 | | | | | |
| ATRI38354 | -4.340 | | | | | |
| ATRI216267 | -3.603 | | | | | |
| ATRI94986 | -4.166 | | | | | |
| ATRI38554 | -4.525 | | | | | |

2.2. In Vitro Cytotoxicity and Anti-SARS-COV-2 Activity of *A. paniculate*

The percentage of cell viability for *A. paniculate* was 103.05 and 83.53 on 24th and 48th hour of treatment respectively. Meanwhile, the percentage of cell viability for Remdesivir was 99.23 and 94.37 on 24th and 48th hour of treatment respectively. *A. paniculate* has demonstrated promising Anti-SARS-COV-2 activity with 99.9% and 99.8% inhibition of E and N gene respectively at 48 hr of treatment. Whereas, Remdesevir has shown 99.8 and 99.89% inhibition of E and N gene respectively at 48 hr of treatment.

2.3. In Vitro IC50 Estimation

Figure 2A:
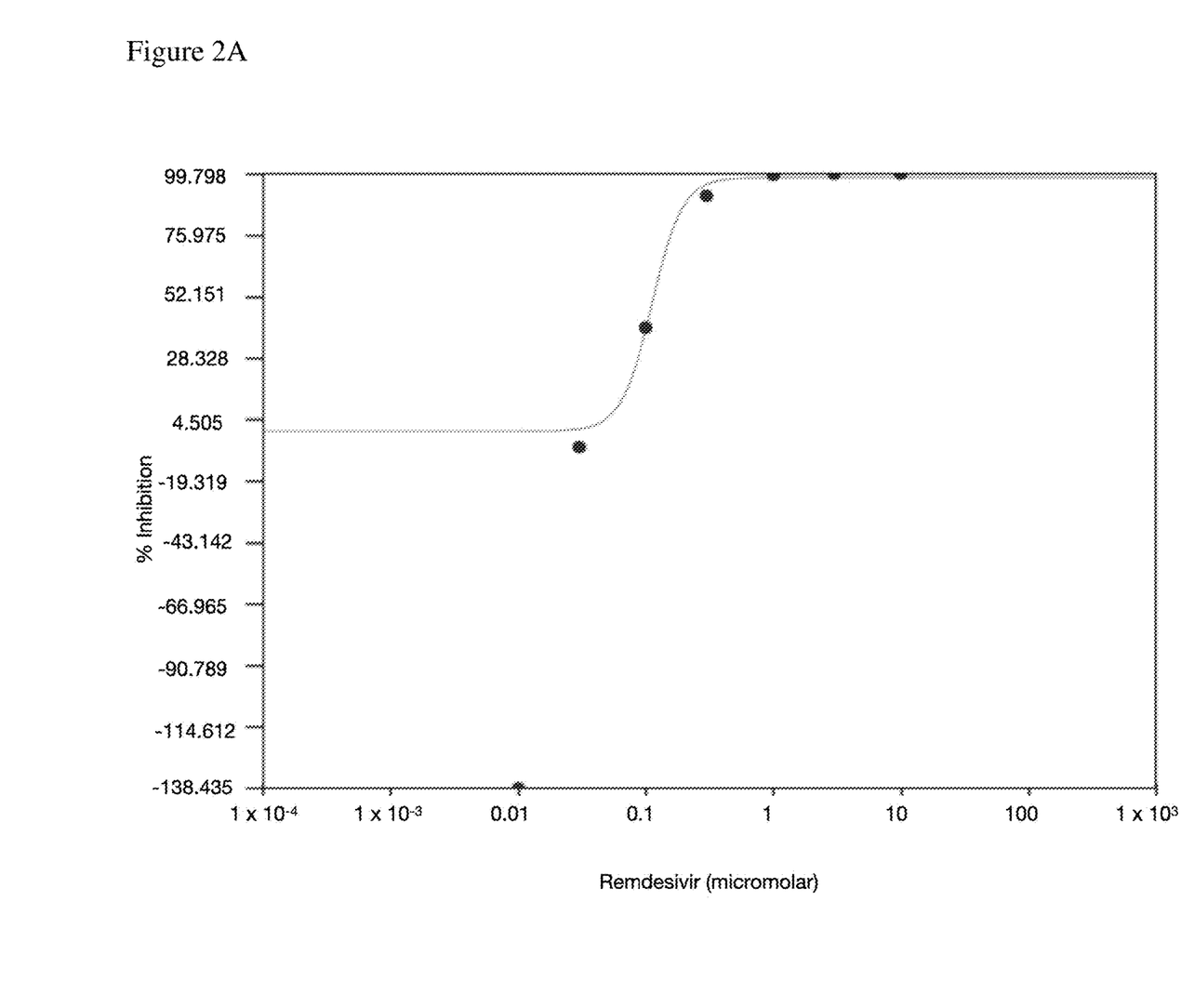
FIG. 2A illustrates dose dependent response of Remdesivir for SARS-COV-2 N gene in accordance with embodiments of the present invention.
Figure 2B:
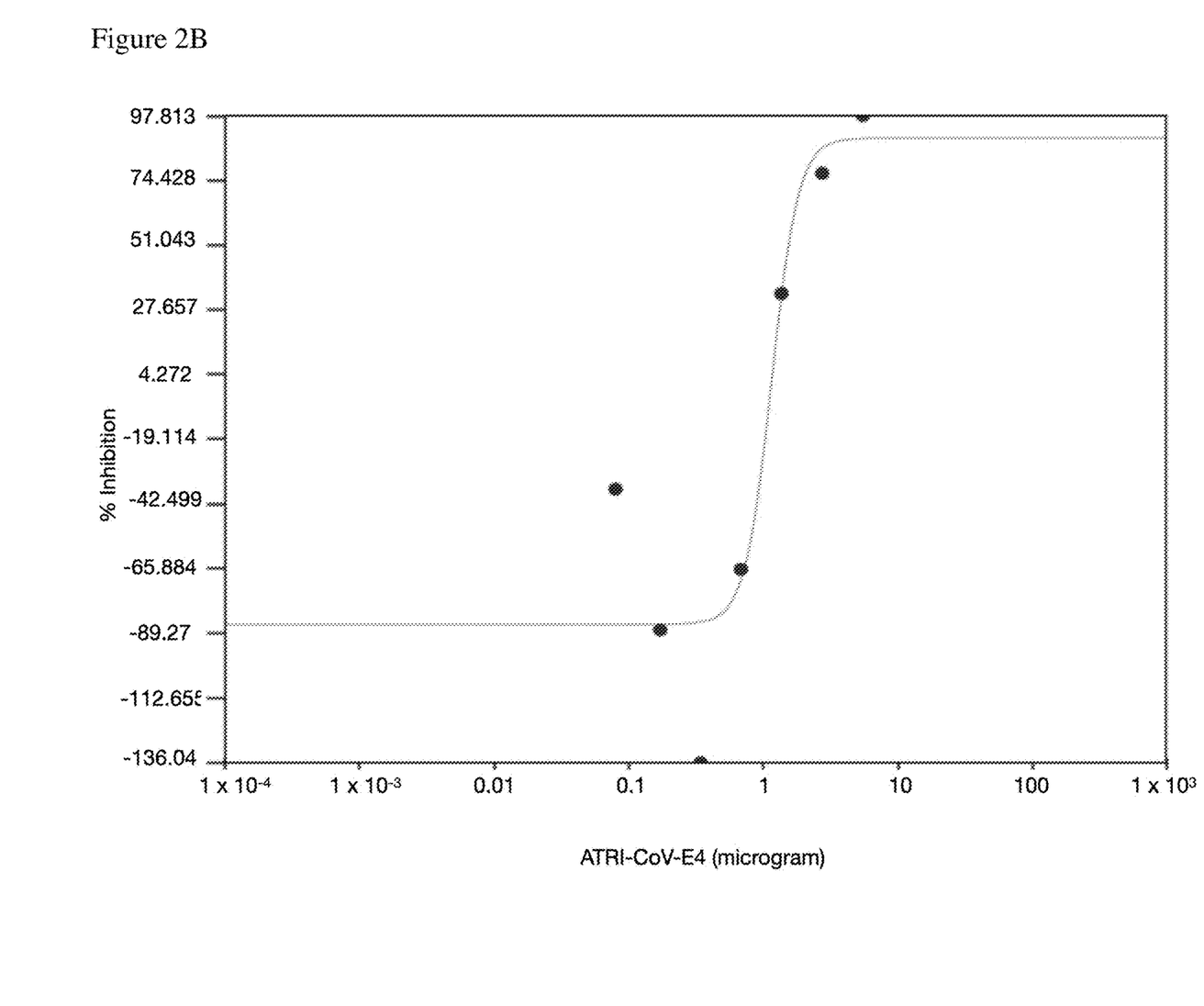
FIG. 2B illustrates dose dependent response of *Andrographis paniculata* for SARS-COV-2 N gene in accordance with embodiments of the present invention.

The seven point IC50 determination performed for ATRI-CoV-E4, using Remdesivir as standard control. The result of *A. paniculate* found consistent with an IC50 1.18 μg and 1.16 μg for E gene and N gene respectively while, an IC50 of Remdesivir was 0.15 μM and 0.11 μM for E gene and N gene respectively as shown in FIGS. 1 and 2.

3.4. In Vivo Toxicity 3.4.1. Observations

Clinical Observation

Clinical signs were observed in all the days and the signs are presented in the Table 3.

Mortality & Morbidity and Gross Pathology

The results of clinical signs, mortality & morbidity, and gross pathology of this study are given in the Table 3.

Gross Pathology Examination

Gross pathology observations of vital organs of the animals at the end of the experiment are presented in the Table 3.

TABLE 3

Results of Clinical signs, Mortality & Morbidity, and Gross pathology

| Date | Dose concentration | Animal No. | Clinical Signs | Mortality & Morbidity | Gross pathology |
|---|---|---|---|---|---|
| Rats | | | | | |
| 24 Aug. 2020 | 2000 mg/kg | 1 | N | Nil | NAD |
| | | 2 | N | Nil | NAD |
| | | 3 | N | Nil | NAD |
| Mice | | | | | |
| 24 Aug. 2020 | 2000 mg/kg | 1 | N | Nil | NAD |
| | | 2 | N | Nil | NAD |
| | | 3 | N | Nil | NAD |

Normal = N,
NAD = No Abnormality Detected
* Additional results can be discussed if necessary In another embodiment of the present invention, the preferred mode is administered orally, in another embodiment, a unit dosage form comprises tablets, capsules, lozenges, chewable tablets, suspensions, emulsions and the like. In certain embodiments, tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. In certain embodiments, the selection of carrier components depends on secondary considerations like taste, cost, and shelf stability, which are 10 not critical for the purposes of this invention, and can be readily made by a person skilled in the art.

I claim:

1. A pharmaceutical formulation for inhibition of SARS-COV-2, comprising:
   i. active ingredients consisting of:
      200 mg-600 mg of *Centella asiatica*;
      100 mg-400 mg of *Withania somnifera*;
      100 mg-400 mg of *Andrographis paniculate*; and
   ii. inert ingredients consisting essentially of:
      1 mg-60 mg of starch;
      1 mg-50 mg of magnesium stearate; and
      1 mg-50 mg of polyvinylpyrrolidone-K 30 (PVP K 30),
   wherein the pharmaceutical formulation is formulated for oral administration.

2. The pharmaceutical formulation of claim 1, wherein the *Centella asiatica*, the *Withania paniculate* and the *Andrographis paniculate* are the principal ingredient.

3. The pharmaceutical formulation of claim 1, wherein the pharmaceutical formulation is for one or more capsules ranging between 300 mg to 1000 mg.

4. A pharmaceutical formulation provided as a capsule, comprising:
   i. active ingredients consisting of:
      200-600 mg of *Centella asiatica*;
      100-400 mg of *Withania somnifera*;
      100-400 mg of *Andrographis paniculate*;
   ii. inert ingredients consisting essentially of:
      10-20 mg of polyvinylpyrrolidone-K 30 (PVP K 30); and
      10-20 mg of acrylic polymer;
   wherein the capsule does not exceed 1000 mg, is formulated for oral administration, and optionally includes 1-50 mg of magnesium stearate.

5. The pharmaceutical formulation of claim 1, consisting essentially of:
   200 mg-600 mg of *Centella asiatica*;
   100 mg-400 mg of *Withania somnifera*;
   100 mg-400 mg of *Andrographis paniculate*;
   1 mg-60 mg of starch;
   1 mg-50 mg of magnesium stearate; and
   1 mg-50 mg of polyvinylpyrrolidone-K 30 (PVP K 30).

* * * * *